(12) United States Patent
Pereswetoff-Morath et al.

(10) Patent No.: US 9,980,959 B2
(45) Date of Patent: May 29, 2018

(54) METHOD AND COMPOSITION FOR TREATING RHINITIS

(75) Inventors: Lena Pereswetoff-Morath, Stockholm (SE); Anders Carlsson, Stockholm (SE)

(73) Assignee: Biolipox AB, Stockholm (SE)

( * ) Notice: Subject to any disclaimer, the term of this patent is extended or adjusted under 35 U.S.C. 154(b) by 656 days.

(21) Appl. No.: 13/444,381

(22) Filed: Apr. 11, 2012

(65) Prior Publication Data

US 2013/0039969 A1   Feb. 14, 2013

Related U.S. Application Data

(63) Continuation of application No. 10/571,330, filed as application No. PCT/GB2005/001758 on May 6, 2005, now abandoned, which is a continuation-in-part of application No. 10/842,433, filed on May 11, 2004, now abandoned.

(51) Int. Cl.
A61K 9/127   (2006.01)
A61K 31/495  (2006.01)
A61K 9/00    (2006.01)

(52) U.S. Cl.
CPC .......... *A61K 31/495* (2013.01); *A61K 9/0043* (2013.01); *A61K 9/0048* (2013.01); *A61K 9/127* (2013.01); *Y10S 977/906* (2013.01); *Y10S 977/907* (2013.01)

(58) Field of Classification Search
CPC .................................................... A61K 9/127
USPC ......................................................... 424/450
See application file for complete search history.

(56) References Cited

U.S. PATENT DOCUMENTS

| | | | |
|---|---|---|---|
| 4,427,649 A | 1/1984 | Dingle et al. | |
| 4,839,175 A | 6/1989 | Guo et al. | |
| 5,049,388 A | 9/1991 | Knight et al. | |
| 5,141,674 A | 8/1992 | Leigh | |
| 5,374,548 A * | 12/1994 | Caras | 424/450 |
| 5,422,120 A | 6/1995 | Kim | |
| 5,498,420 A | 3/1996 | Mentrup et al. | |
| 5,569,464 A | 10/1996 | Endo et al. | |
| 5,783,566 A * | 7/1998 | Mislick | 514/44 R |
| 5,952,361 A * | 9/1999 | Dias Nahoum | 514/396 |
| 6,226,393 B1 | 5/2001 | Grunkin et al. | |
| 2001/0006660 A1 * | 7/2001 | Lagace et al. | 424/400 |
| 2002/0064524 A1 | 5/2002 | Ceve | |
| 2002/0102293 A1 | 8/2002 | Sachse et al. | |
| 2003/0054030 A1 | 3/2003 | Gordon | |
| 2003/0124180 A1 * | 7/2003 | Ebert et al. | 424/450 |
| 2003/0144336 A1 * | 7/2003 | Chen et al. | 514/400 |
| 2004/0192601 A1 * | 9/2004 | Corvera et al. | 514/12 |
| 2004/0198743 A1 * | 10/2004 | Hey et al. | 514/255.04 |
| 2004/0224011 A1 * | 11/2004 | Rodrigueza et al. | 424/450 |
| 2005/0084453 A1 * | 4/2005 | Ueda et al. | 424/9.45 |
| 2005/0112199 A1 | 5/2005 | Padval et al. | |

FOREIGN PATENT DOCUMENTS

| | | |
|---|---|---|
| EP | 0 249 561 A2 | 12/1987 |
| EP | 0 605 203 A2 | 7/1994 |
| EP | 1 438 955 A1 | 7/2004 |
| WO | WO 87/01586 A1 | 3/1987 |
| WO | WO 87/07506 A1 | 12/1987 |
| WO | WO 88/01862 A1 | 3/1988 |
| WO | WO 90/14105 A1 | 11/1990 |
| WO | WO 95/20944 A1 | 8/1995 |
| WO | WO 97/01337 A1 | 1/1997 |
| WO | WO 97/46243 A1 | 12/1997 |
| WO | WO 98/00111 A1 | 1/1998 |
| WO | WO 98/48839 A1 | 11/1998 |
| WO | WO 98/58629 A2 | 12/1998 |
| WO | WO 00/38681 A1 | 7/2000 |
| WO | WO 02/45688 A2 | 6/2002 |
| WO | WO 03/049770 A1 | 6/2003 |
| WO | WO 03/097100 A1 | 11/2003 |
| WO | WO 03/105805 A1 | 12/2003 |
| WO | WO 2005/039533 A1 | 5/2005 |

OTHER PUBLICATIONS

Elzainy, A.A.W.e tal in AAPS PharmSci. 5 (4), pp. 1-8 (Dec. 2003).*
Iwanaga, K., Biol. Pharm. Bull. 23 (3), pp. 323-326 (2000_.*
Van Balen, G.P. et al., "Lipophilicity Behaviour of the Zwitterionic Antihistamine Cetirizine in Phophatidyleholine Liposomes/Water Systems," *Pharmaceutical Research*, 18(5):2001-2005 (2001).
Fischer, M.J.E. et al., "Inhibition of Mediator Release in RBL-2H3 Cells by Some $H_1$-Antagonist Derived Anti-allergic Drugs: Relation to Lipophilicity and Membrane Effects," *Inflamm Res* 44(2):92-97 (1995).
Vemuri, S. et al., "Preparation and Characterization of Liposomes as Therapeutic Delivery Systems: A Review," *Pharmaceutica Acta Helvetiae* 70(2):95-111 (1995).
Iwanaga, K. et al., "Usefulness of Liposomes as an Intranasal Dosage Formulation for Topical Drug Application," *Biol. Pharm. Bull.* 23(3):323-326 (2000).
Desai, T.R. et al., "A Facile Method of Deliver of Liposomes by Nebulization," *Journal of Controlled Release* 84(1-2):69-78 (2002).
Elzainy, A A.W. et al., "Cetirizine From Topical Phosphatidylcholine-Hydrogenated Liposomes: Evaluation of Peripheral Antihistaminic Activity and Systemic Absorption in a Rabbit Model," *AAPS Journal* 6(3) Article 18 (2004).
Francillon, C. et al., "Effect of Nasal Spray of Cetirizine in a Nasal Provocation Test with Allergen," *J Allergy Clin Immunol* 91(2):258 (1993).
Ghosh, S.K. et al., "Effect of Cetirizine on Exercise Induced Asthma," *Thorax* 46(4):242-244 (1991).
Clement, P. et al., "Dose-ranging, Placebo-controlled Study of Cetirizine Nasal Spray in Adults with Perennial Allergic Rhinitis," *Allergy* 49(8):668-672 (1994).
Türker, S. et al., "Nasal Route and Drug Delivery Systems," *Pharm World Sci* 26:137-142 (2004).
Elzainy, AAW et al., "Hydroxyzine- and Cetirizine-Loaded Liposomes: Effect of Duration of Thin Film Hydration, Freeze-Thawing, and Changing Buffer pH on Encapsulation and Stability," *Drug Development and Industrial Pharmacy* 31:281-291 (2005).

(Continued)

*Primary Examiner* — Isaac Shomer
(74) *Attorney, Agent, or Firm* — LeClairRyan, PLLC

(57) ABSTRACT

There is provided pharmaceutical compositions for the treatment of rhinitis by, for example, nasal or ocular administration comprising zwitterionic cetirizine, a polar lipid liposome and a pharmaceutical acceptable aqueous carrier. The compositions are preferably homogeneous in their nature.

3 Claims, No Drawings

(56) References Cited

OTHER PUBLICATIONS

Carlsson A et al., "Galactolipids—A New Tool in Drug Formulation" *Proceedings of the 21st World Congress of the International Society for Fat Research (ISF)*, The Hague, Oct. 1995: PJ Barnes & Associates: Bridgewater, 2:259-262 (1996).

Simons, K.J. et al., "Effect of Different Phospholipids on the Stability of Liposomal Formulations Containing Cetirizine," *The AAPS Journal* 5(4) Abstract T3272 (2003).

Elzainy, A.A. et al., "Evaluation of Peripheral Antihistaminic Activity and Systemic Absorption of Cetirizne from Various Topical Phospholipid Liposomal Formulations in a Rabbit Model," *The AAPS Journal* 4(4) Abstract T3256 (2002).

Kikuchi, H. et al., "Possibility of Heat Sterilization of Liposomes," *Chem. Pharm. Bull.*, 39(4): 1018-1022 (Apr. 1991).

Mishina, E.V. et al., "Inhibition of Rat Splenocyte Proliferation with Methylprednisolone: In Vivo Effect of Liposomal Formulation," *Pharmaceutical Research*, 11(6): 848-854 (1994) (Month Not Available).

Gursoy, A. et al., "Preparation, Characterization and Anti-Inflammatory Effect of Defibrotide Liposomes," *Pharmazie*, 48(7): 549-550 (1993) (Month Not Available).

Paulussen, J.J.C. et al., "Influence of the Antiallergic Drug Oxatomide and Derivatives on Membrane Structures: Relation with Inhibition of Calcium Influx in Rat Basophilic Leukemia Cells," *Biochemical Pharmacology*, 57(5): 503-510 (Jan. 1999).

Ahmed, M. et al., "Partitioning and Efflux of Phenothiazines from Liposomes," *Biochemical Pharmacology*, 29(17) : 2361-2365 (1980) (Month Not Available).

Elzainy, A.A. et al., "Evaluation of Peripheral Antihistaminic Activity and Systemic Absorption of Cetirizine from Various Topical Phospholipid Liposomal Formulations in a Rabbit Model," *AAPS Pharsci [Electronic resource]*, 5(4): E28 (2003) (Month Not Available).

Welch, M.J., "Epitomes: Important Advances in Clinical Medicine," *The Western Journal of Medicine*, 154(4): 455 (1991) (Month Not Available).

Elzainy, A.A.W. et al., "Cetirizine from Topical Phosphatidylcholine Liposomes: Evaluation of Peripheral Antihistaminic Activty and Systemic Absorption in a Rabbit Model," *Biopharmaceutics & Drug Disposition*, 25(8): 359-366 (Oct. 2004).

Betageri, G.V. et al., *Liposome Drug Delivery Systems*, Technomic Publishing AG, Basel, Switzerland (1993) Cover, Title Page and Table of Contents Only.

Elzainy, A.A.W. et al., "Hydroxyzine from Topical Phospholipid Liposomal Formulations: Evaluation of Peripheral Antihistaminic Activity and Systemic Absorption in a Rabbit Model," *AAPS PharmSci*, 5(4): 1-8 (Dec. 2003).

Desai, T.R. et al., "A Novel Approach to the Pulmonary Delivery of Liposomes in Dry Powder Form to Eliminate the Deleterious Effects of Milling," *Journal of Pharmaceutical Sciences*, 91(2): 482-491 (Feb. 2002).

*New Techniques for Making Novel Pharmaceutical Compositions*, 1st Edition, Public Health Publisher, pp. 116 (1998) (in Chinese Language Only).

"New Techniques and New Dosage Forms of Drugs," Bin, Lu (ed.), People's Medical Publishing House:Beijing (1998), 3 pgs., (English Translation).

\* cited by examiner

METHOD AND COMPOSITION FOR TREATING RHINITIS

RELATED APPLICATION(S)

This application is a continuation of U.S. patent application Ser. No. 10/571,330, now abandoned, which is the U.S. National Stage of International Application No. PCT/GB2005/001758, filed May 6, 2005, published in English, now expired, which is a continuation-in-part of and claims priority under 35 U.S.C. § 119 or 365 to U.S. patent application Ser. No. 10/842,433, filed May 11, 2004, now abandoned. The entire teachings of the above application(s) are incorporated herein by reference.

FIELD OF THE INVENTION

This invention relates to a method for treating rhinitis, and to a corresponding pharmaceutical composition.

BACKGROUND AND PRIOR ART

Allergic and non-allergic rhinitis are common disorders affecting about 30% of the population. Rhinitis has a considerable impact on quality of life. In fact, rhinitis is regarded to affect the quality of life more so than, e.g., asthma.

Hay fever and perennial allergic rhinitis are characterised by sneezing, rhinorrhea, nasal congestion, pruritus, conjunctivitis and pharyngitis. In perennial rhinitis, chronic nasal obstruction is often prominent and may extend to eustachian tube obstruction.

Oral or local antihistamines are first line treatments, and nasal steroids second line treatments for rhinitis. For most patients, topical corticosteroids and long acting antihistamine agents provide significant relief of symptoms. Antihistamines may also affect non-immunologically (non-IgE) mediated hypersensitivity reactions such as non-allergic rhinitis, exercise induced asthma, cold urticaria, and non-specific bronchial hyperreactivity.

Cetirizine dihydrochloride, [2-{4-[(4-chlorophenyl)-phenylmethyl]-1-piperazinyl}ethoxy]acetic acid is an orally and locally active, potent, long acting peripheral histamine $H_1$ receptor antagonist. Cetirizine is one of the most widely used second generation antihistamines for the treatment of rhino-conjunctivitis and urticaria. It is effective, well tolerated and safe when used orally in a dose of 10 mg daily. Sedation and dry mouth do however occur as side effects in orally treated patients. Cetirizine is also approved in children for the treatment of rhinitis.

The main clinical affects of antihistamines include reduced sneezing and rhinorrhea. However, reduction of nasal blockage appears to be less responsive.

Local administration of antihistamines (such as azelastine and levocabastine) has advantages, including rapid onset of action and fewer side effects. At present, however, cetirizine dihydrochloride is not an approved medicine for local administration, although it has been administered in that manner in clinical trials.

In one trial (Francillon C, Pécoud A. *Effect of nasal spray of cetirizine in a nasal provocation test with allergen*. J Allergy Clin. Immunol. 1993:91, Suppl. 2:258 (abstract)), cetirizine nasal spray was found to reduce symptoms and increase nasal peak flow after an allergen challenge. Further, in exercise-induced asthma, a good protective effect was seen when cetirizine mist was administered to the lung with a nebulizer (Ghosh S K, De Vos C, McIlroy I, Patel K R. *Effect of cetirizine on exercise induced asthma*, Thorax 1991 April; 46 (4), 242-4).

Some effect was seen on symptoms when cetirizine (presumably as the dihydrochloride) was given as a nasal spray in patients with perennial allergic rhinitis. Concentrations of 0.625, 1.25, and 2.5 mg/mL of cetirizine were sprayed three times a day for two weeks (Clement P, Roovers M H, Francillon C, Dodion P. *Dose-ranging, placebo-controlled study of cetirizine nasal spray in adults with perennial allergic rhinitis*, Allergy 1994 September; 49 (8), 668-72). The most common side effects were related to nasal events, although no difference in incidence between the placebo and the cetirizine-treated groups was seen. However, the authors of this article speculated therein that local irritation had an adverse effect on treatment efficacy.

Indeed, due to the irritation of the nasal mucosa by cetirizine, it has been found to be necessary to decrease its immediate exposure in nasal administration. In European Patent No. EP 605 203 B1, it has been reported that this can be achieved by providing cetirizine in form of a composition containing cyclodextrin.

Liposomes (also known as lipid vesicles) are colloidal particles that are prepared from polar lipid molecules derived either from natural sources or chemical synthesis. Such spherical, closed structures composed of curved lipid bilayers, are typically used to entrap drugs, which are often cytotoxic, in order to reduce toxicity and/or increase efficacy. Liposome-entrapped drug preparations are often provided in a dry (e.g. freeze-dried) form, which is subsequently reconstituted with an aqueous solution immediately prior to administration. This is done in order to minimise the possibility of leakage of e.g. cytotoxic drug into aqueous solution and thereby reducing the entrapping effect of the liposome.

Liposomes have also been employed to encapsulate various drug compounds for delivery via the nasal route, in order to improve bioavailability or as an adjuvant. Drugs that may be mentioned include tetanus toxoid vaccine, insulin, desmopressin and diphenhydramine hydrochloride (see Türker et al, *Review Article: Nasal Route and Drug Delivery Systems*, Pharm, World Sci., 2004; 26, 137-142 and the references cited therein), as well as ciprofloxacin, CM3 and salbutamol (see Desai et al, *A Facile Method of Delivery of Liposomes by Nebulization*, J. Control. Release, 2002; 84, 69-78).

Liposome-entrapped cetirizine has also been administered topically to evaluate peripheral antihistaminic activity and systemic absorption in a rabbit model (Elzainy et al, *Cetirizine from Topical Phosphatidylcholine-Hydrogenated Liposomes*, The AAPS Journal, 2004; 6, 1-7. See also Drug Development and Industrial Pharmacy, 2005; 31, 281-291).

The lipophilic behaviour of the cationic (wherein the anion is chloride), zwitterionic, and anionic forms of cetirizine in buffered aqueous phosphatidylcholine liposome systems containing from about 1 to 33.5 mg/mL of phospholipid has also been studied (Plemper van Balen G at al., *Lipophilicity behaviour of the zwitterionic antihistamine cetirizine in phosphatidylcholine liposomes/water systems*, Pharm. Res. 2001; 18, 694-701). The aim with the study, in which separate solutions of PBS-diluted egg phosphatidylcholine liposomes were poured into separate compartments of dialysis cells, was to gain insight into the mechanism of interaction of the various electrical species of cetirizine and other drugs with liposomal membranes. The zwitterionic form of cetirizine, which dominates in the pH range of from about pH 4 to about pH 7, and even from about pH 3 to about pH 8, was considered by the authors of this article to be prevented from entry into the liposomal membrane by rendering the formation of lipophilic folded conformers of cetirizine more difficult. In this respect, cetirizine was not entrapped in liposomal membranes for delivery of drug to patients.

To the applicant's knowledge there is no prior disclosure or suggestion in the art of a homogeneous pharmaceutical composition comprising zwitterionic cetirizine, a polar lipid liposome and a pharmaceutical acceptable aqueous carrier.

Surprisingly, we have found that the irritation normally associated with (e.g. nasal) administration of cetirizine may be reduced by way of use of just such a composition.

According to the invention, there is provided pharmaceutical compositions suitable for the treatment of rhinitis by, for example, nasal or ocular administration comprising zwitterionic cetirizine, a polar lipid liposome and a pharmaceutical-acceptable aqueous carrier, which compositions are referred to hereinafter as "the compositions of the invention".

The skilled person will appreciate that zwitterionic cetirizine is employed in compositions of the invention in a pharmacologically-effective amount (vide infra). The term "pharmacologically-effective amount" refers to an amount of cetirizine, which is capable of conferring the desired therapeutic effect on a treated patient, whether administered alone or in combination with another active ingredient. Such an effect may be objective (i.e. measurable by some test or marker) or subjective (i.e. the subject gives an indication of, or feels, an effect).

By "pharmaceutical compositions" we include compositions that are suitable for use in direct administration to mammals, and especially humans. In this respect, the term is intended to encompass formulations that include only components that are regarded in the art as suitable for administration to mammalian, and especially human, patients. In the context of the present invention, the term may also mean that the compositions of the invention are in a form of a liquid that is ready-to-use, directly from the shelf, and not a formulation in which drug is encapsulated inside liposomes requiring reconstitution shortly prior to administration in order to avoid leakage of drug from liposomes into an aqueous carrier.

The compositions of the invention are preferably homogeneous. By "homogenous" we include not only that the compositions of the invention comprise liposomes dispersed evenly throughout the aqueous carrier, but further that the active ingredient is distributed throughout the whole composition in a substantially similar concentration in the relevant aqueous medium, whether that medium is located inside or outside of the liposomal structures. By "substantially similar", we include that the concentration may vary by about ±50%, such as about ±40%, preferably about ±30%, more preferably about ±20% and particularly about ±10% (when comparing concentrations inside and outside of the liposomal structures) at room temperature and atmospheric pressure. Drug concentration profiles may be measured by standard techniques known to the skilled person, such as $^{31}$P-NMR. For example, a standard in situ probing technique, or a technique that involves separation of the liposomal fraction from the free aqueous carrier and measurement of the amount/concentration of drug associated with each fraction may be employed. Separation may be accomplished by centrifugation, dialysis, ultrafiltration, or gel filtration.

It is preferred that the compositions of the invention further include a pharmaceutically-acceptable buffer capable of providing a pH of from about pH 4 (e.g. 4.0) to about pH 8 (e.g. 8.0), preferably from about pH 5 (e.g. 5.0) to about pH 7 (e.g. 7.0). Appropriate buffers include those that will not interfere with the formation of liposomes, such as a phosphate (e.g. disodium phosphate, dipotassium phosphate, sodium dihydrogen phosphate, potassium dihydrogen phosphate or phosphoric acid plus base), citrate (e.g. sodium citrate or citric acid plus base), or acetate buffer (e.g. sodium acetate or acetic acid plus base), which is capable of maintaining a pH within the above-specified ranges. Buffers may be employed in an amount that is suitable to provide for the above-mentioned effects and such will be appreciated by the skilled person without recourse to inventive input. Appropriate quantities are for example in the range of about 1 mg/mL to about 30 mg/mL.

Any pharmaceutically-acceptable salt of cetirizine as well as the free base form thereof may be used in the manufacture of compositions of the invention. Preferred salts include chloride salts, hydrochloride (e.g. dihydrochloride) salts and, more particularly, nitrate salts of cetirizine, most preferably cetirizine dinitrate.

The amount of cetirizine or salt thereof that may be employed in preparation of compositions of the invention may be determined by the physician, or the skilled person, in relation to what will be most suitable for an individual patient. This is likely to vary with the severity of the condition that is to be treated, as well as the species, age, weight, sex, renal function, hepatic function and response of the particular patient to be treated. It is preferred however that the compositions of the invention comprise cetirizine or a salt thereof in an amount of from about 1 mg/mL to about 30 (e.g. about 25, such as about 23) mg/mL calculated on the zwitterionic form, preferably in an amount of from about 5.5 mg/mL to about 22 mg/mL. A further preferred range is between about 6 mg/mL and about 15 mg/mL, such as about 8 mg/mL to about 12 mg/mL.

In such a case, the total amount of active ingredient that may be present may be sufficient to provide a daily dose of drug per unit dosage that is in the range about 4 mg to about 20 mg, such as about 5 mg to about 15 mg, more preferably about 7 mg to about 12 mg and most preferably about 8 mg to about 10 mg. The skilled person will appreciate that compositions of the invention may be dosed once or more times daily in one or more administrations in order to provide the aforementioned daily dose.

The above-mentioned dosages are exemplary of the average case; there can, of course, be individual instances where higher or lower dosage ranges are merited, and such are within the scope of this invention.

The term "liposome" will be well understood by those skilled in the art to include a structure consisting of one or more concentric spheres of polar lipid bilayers separated by water or aqueous buffer compartments.

Liposomes may be prepared by various methods using solvents, reduced pressure, two-phase systems, freeze drying, sonication etc. described, for instance, in *Liposome Drug Delivery Systems*, Betageri G V et al., Technomic Publishing AG, Basel, Switzerland, 1993, the relevant disclosures in which document are hereby incorporated by reference.

The term "polar lipid" will be well understood by the skilled person to include any lipid with a polar head-group and two fatty acid residues, which is capable of forming liposomes.

Polar lipids, such as those described hereinafter, may be of a natural and/or a synthetic/semi-synthetic origin. Mixtures of natural and synthetic/semi-synthetic polar lipids may also be employed in compositions of the invention.

Polar lipids that may be employed in compositions of the invention may thus be based on, for example, phospholipids, and in particular phosphatidylcholine (PC), phosphatidylglycerol (PG), phosphatidylinositol (PI), phosphatidic acid (PA), phosphatidylserine (PS), or mixtures thereof.

Phospholipids that may be employed in compositions of the invention comprise polar and non-polar groups linked to a backbone entity carrying hydroxyl groups, such as glycerol.

Phospholipids may also be represented by the general formula I

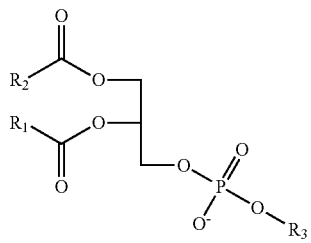

wherein $R_1$ and $R_2$ independently represent a saturated or unsaturated (e.g. alkenyl), branched or straight chain alkyl group having between 7 and 23 carbon atoms, preferably between 11 and 19 carbon atoms; and $R_3$ represents an amide or ester bonding group, such as
—$CH_2$—$CH(OH)$—$CH_2OH$ (phosphatidylglycerol),
—$CH_2$—$CH_2$—$N(CH_3)_3$ (phosphatidylcholine),
—$CH_2$—$CH_2$—$NH_2$ (phosphatidylethanolamine),
—H (phosphatidic acid), or
—$CH_2$—$CH(NH_2)$—COOH (phosphatidylserine).

The phospholipid may be of natural origin. Natural phospholipids are preferably membrane lipids derived from various sources of both vegetable (e.g. rapeseed, sunflower, etc., or, preferably, soybean) and animal origin (e.g. egg yolk, bovine milk, etc.). Phospholipids from soybean, a major source of vegetable phospholipids, are normally obtained from the by-products (i.e. lecithins) in the refining of crude soybean oil by the degumming process. The lecithins are further processed and purified using other physical unit operations, such as fractionation and/or chromatography. Other phospholipids may be obtained, for example, by pressing various suitable seeds and grains, followed by solvent extraction and then further processing as described above, Phospholipids of natural origin that may be mentioned include for example those that are available under the tradenames Lipoid S75, Lipoid S100 and Lipoid S75-3N (Lipoid GmbH, Germany), which are all blends of several different phospholipids that are found in soybean.

The phospholipid may alternatively be of synthetic or semi-synthetic origin (i.e. prepared by chemical synthesis). For example, a multi-step chemical synthetic approach may be used in order to obtain the key phospholipid intermediates, 1,2-diacylglycerol, from (S)-1,2-isopropylideneglycerol, the latter providing the glycerol backbone that is characteristic of phospholipids. 1,2-Diacetylated phospholipids may then be obtained when the corresponding polar head group is attached via chemical synthesis to the 1,2-diacylglycerol intermediate. Generally, however, the origin of glycerol and the fatty acids used in the various steps may be of both natural and synthetic origin. Synthetic and/or semi-synthetic phospholipids that may be mentioned include dilaurylphosphatidylcholine (DLPC), dimyristolphosphatidylcholine (DMPC), dipalmitoylphosphatidylcholine (DPPC), dilaurylphosphatidylglycerol (DLPG), dimyristolphosphatidylglycerol (DMPG), dioleoylphosphatidylcholine (DOPC) and dioleoylphosphatidylglycerol (DOPG).

The polar lipid may alternatively comprise or, more preferably, consist of a glycolipid. In the context of the present invention, the term "glycolipid" designates a compound containing one or more monosaccharide residues bound by a glycosidic linkage to a hydrophobic moiety such as an acylglycerol, a sphingoid or a ceramide (N-acylsphingoid).

A glycolipid may be a glycoglycerolipid. In the context of the present invention, the term "glycoglycerolipid" designates a glycolipid containing one or more glycerol residues. According to a preferred aspect of the invention, the glycoglycerolipid comprises, or consists of, galactoglycerolipid, more preferably a digalactosyldiacylglycerol of the general formula II,

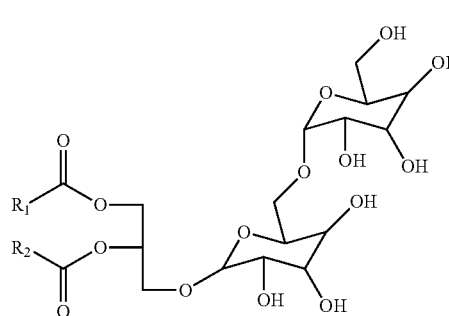

wherein $R_1$ and $R_2$ are as hereinbefore defined.

The glycolipid may alternatively be a glycosphingolipid. In the context of the present invention, the term "glycosphingolipid" designates a lipid containing at least one monosaccharide residue and either a sphingoid or a ceramide. The term may thus comprise neutral glycophingolipids, such as mono- and oligoglycosylsphingoids as well as oligo- and, more preferably, monoglycosylceramides. The teen additionally comprises acidic glycosphingolipids such as sialoglycosphingolipids, uronoglycosphingolipids, sulfoglycosphingolipids, phosphoglycosphingolipids, and phosphonoglycosphingolipids. The glycosphingolipid can be ceramide, monohexosylceramide, dihexosylceramide, sphingomyelin, lysosphingomyelin, sphingosine, or a mixture thereof. Preferably the glycosphingolipid is sphingomyelin or products derived therefrom. The sphingomyelin content is preferably established by chromatographic methods, Sphingomyelin may be extracted from milk, preferably bovine milk, brain, egg yolk or erythrocytes from animal blood, preferably sheep. For the avoidance of doubt, synthetic and semi-synthetic sphingolipids are comprised by the invention.

The glycolipid may alternatively be a glycophosphatidylinositol. In the context of the present invention, the term "glycophosphatidylinositol" designates a glycolipid containing saccharides glycosidically linked to the inositol moiety of phosphatidylinositols.

Preferred glycolipids include digalactosyldiacylglycerol (DGDG).

Preferred polar lipids (such as phospholipids) are those that swell to a measurable degree in water and/or those which are capable of spontaneous liposome formation.

If the polar (e.g. phospho-) lipid does not swell spontaneously in water, the skilled person will appreciate that it is nevertheless possible to obtain liposomes by adding a more polar, swellable (e.g. phospho-) lipid, such as an anionic (e.g. phospho-) lipid (e.g. phosphatidylglycerol).

Liposome formation may be performed at above about 0° C. (e.g. room temperature) if the phase transition temperature of the acyl chains (chain melting; gel-to-liquid crystals) is below the freezing point of water.

Whichever polar lipid substance (or combination thereof) is used, suitable total amounts/concentrations of lipid(s) that may be employed in preparation of a composition of the invention are in the range of about 10 mg/mL to about 120 mg/mL. Compositions of the invention that may be mentioned include those in which, when the polar lipid comprises phospholipid (whether in combination with another lipid or otherwise), the amount of phospholipid(s) in the composition is from about 10 (e.g. about 17, such as about 20) mg/mL to about 120 mg/mL, more preferably from about 25 (e.g. about 35) mg to about 100 (e.g., about 70, such about 50, e.g. about 40) mg/mL.

Compositions of the invention may also comprise an antioxidant, such as α-tocopherol, ascorbic acid, butylated hydroxyanisole, butylated hydroxytoluene, citric acid, fumaric acid, malic acid, monothioglycerol, propionic acid, propyl gallate, sodium ascorbate, sodium bisulfite, sodium metabisulfite, potassium metabisulfite, sodium sulfite, tartaric acid or vitamin E.

According to the invention a chelating agent may be used to reduce the metal ion catalysed oxidation of phospholipid and/or cetirizine. Examples of useful chelating agents are ethylenediaminetetraacetic acid (EDTA), ethylenediaminetriacetic acid and diethylenetriaminepentaacetic acid (DTPA). It is also possible to use other agents that protect the composition of the invention and, in particular, any unsaturated fatty acid residues that may be present therein, from oxidation.

The composition of the invention can comprise one or more preservatives. Examples of common preservatives for liquid pharmaceutical compositions are benzalkonium chloride, benzoic acid, butylated hydroxyanisole, butylparaben, chlorbutanol, ethylparaben, methylparaben, propylparaben, phenoxyethanol or phenylethyl alcohol.

In order to retain the composition of the invention at its application site it may also comprise viscosity-increasing agent such as, for instance, hydrophilic polymers like polyethyleneglycol, or crosslinked polyvinylpyrrolidone and/or cellulose derivatives such as hydroxypropylmethyl cellulose. Viscosity increasing agents may also function as protective colloids to physically stabilise the composition of the invention prior to administration.

Compositions of the invention may also comprise flavourings (e.g. lemon, menthol or peppermint powder) and/or sweeteners (e.g. neohesperidin).

Compositions of the invention may also comprise tonicity-modifying agents, such as sodium chloride; potassium chloride, glycerol, glucose, dextrose, sucrose, mannitol, etc.

Optional additives, including buffering agents, preservatives, viscosity-increasing agents, antioxidants, tonicity-modifying agents and chelating agents should be selected, in terms of their identity and the amounts employed, keeping in mind that their detrimental effect on liposome stability should be kept at a minimum. For a given agent this can be ascertained by simple experiments, which are well within the understanding of the skilled person. Suitable amounts of such ingredients are however in the range about 0.01 mg/mL to about 10 mg/mL.

There is also provided a process for preparing compositions of the invention. We have surprisingly found that liposomes may be prepared by direct swelling of the polar lipids in an aqueous medium without the addition of any other excipients such as charged lipids and/or surfactants etc., which are normally required.

According to a further aspect of the invention, there is provided a process for preparing a composition of the invention, which process comprises:
(a) providing a polar lipid or a mixture of polar lipids that is/are swellable in aqueous media;
(b) providing an aqueous solution of cetirizine;
(c) adding the polar lipid or mixture to the aqueous solution with stirring, thereby forming a cetirizine liposome preparation;
(d) optionally adjusting the pH of the preparation to a desired value within the range of from about pH 4 (e.g. 4.0) to about pH 8 (e.g. 8.0), preferably from about pH 5 (e.g. 5.0) to about pH 7 (e.g. 7.0), by adding an acid or a base (e.g. hydrochloric acid and/or sodium hydroxide at an appropriate concentration (e.g. 1M));
(e) optionally adding buffer solution or, more preferably, water or saline to the preparation to obtain a desired final batch volume; and
(f) homogenising the preparation to obtain said pharmaceutical composition.

Solutions/liquids may be purged with nitrogen or argon at a suitable stage in the above process, if and as appropriate.

In the context of the present invention, a lipid may be said to be swellable in aqueous media if, when placed in contact with such a medium, it swells to a measurable degree.

Buffers may preferably be added to the aqueous solution of drug (and/or drug may be added to an aqueous buffer solution) prior to the addition of lipid. This notwithstanding, the person skilled in the art will be aware of the inherent buffering effect of zwitterionic cetirizine.

The formation of the liposomes of the invention may be facilitated by the spontaneous swelling of the polar lipid in water forming a lamellar liquid crystalline phase having a maximum water content of about 35% by weight or higher depending on the nature of the polar lipid, Depending on the lipid or lipid mixture used and other conditions, spontaneous formation of liposomes may be achieved when excess water is added to this lamellar phase. If spontaneous formation is not achieved, the formation of liposomes may be accomplished by the mechanical dispersion step (i.e. the homogenisation step (f) of the above process) of the lamellar liquid-crystalline phase in excess water.

Homogenisation/dispersion methods include vigorous mechanical mixing, for instance by means of an Ultra Turrax® (Jankel & Kühnke, Germany), Shaking, vortexing and rolling may also be performed as part of the homogenisation step of the above process.

A homogeneous size distribution of the liposomes of the invention may be desirable and may be obtained by extrusion through a membrane filter, such as one made of polycarbonate, with a pore size of about 100 nm. Membrane filters may be procured from Avestin Inc., Canada.

A reduced average liposome size and narrowed liposome size distribution may preferably also be obtained when the liposomal dispersion is subjected to high-pressure homogenisation with a suitable homogeniser (Rannie APV, type 7.30 VH, Rannie AS, Denmark) at, for example, between about 300 bar and about 1000 bar, such as between about 400 bar and about 900 bar, e.g. about 500 to about 800 bar for between about 4 and about 8 (e.g. 7, such as 6) cycles.

Surprisingly, we have found that the presence of cetirizine results in a reduction of liposome size. Smaller liposomes are generally advantageous because they are more stable physically and, due to their higher surface area/volume ratio, are more easily resorbed by the mucosa.

We prefer that the diameter of liposomes in compositions of the invention is less than about 200 nm (e.g. between about 40 to about 100 nm), as measured by, for example, laser diffraction or dynamic light scattering, e.g. as described hereinafter.

Furthermore, the above-mentioned process for the preparation of compositions of the invention does not normally require conventional treatment with organic solvents such as chloroform or dichloromethane. However, if two or more membrane lipids are used it may be appropriate and/or necessary to treat them with organic solvent prior to the addition of the aqueous solvent. For example, the lipids may be dissolved in a volatile solvent or solvent mixture, such as chloroform or chloroform/methanol. The solution may then be deposited on the surfaces of a round-bottomed flask as the solvent is removed by rotary evaporation under reduced pressure. An excess volume of aqueous buffer containing the drug may then be added to the dry thin film of lipids, which may then be allowed to swell to form liposomes.

The compositions of the invention are useful in the treatment of any indication for which cetirizine is known to be indicated, including rhinitis. The term "rhinitis" will be understood to include any irritation and/or inflammation of the nose, whether allergic or non-allergic, including seasonal rhinitis (e.g. caused by outdoor agents such as pollen; hay fever) and/or perennial rhinitis (e.g. caused by house dust mites, indoor mold etc), as well as the symptoms thereof.

According to a further aspect of the invention, there is provided a method for the treatment of rhinitis comprising the (e.g. nasal) administration of a pharmacologically-effective amount of a composition of the invention to a person suffering from or susceptible to that disorder.

For the avoidance of doubt, by "treatment" we include the therapeutic treatment, as well as the symptomatic treatment, the prophylaxis, or the diagnosis, of a condition.

The compositions of the invention may be administered by way of a nasal spray, nasal drops and/or eye drops. It is also possible to administer compositions of the invention as a fine mist to the lungs by nebulization. For nasal administration, any state-of-the-art device suitable for producing sprays of aqueous liposomal dispersions may be used.

Wherever the word "about" is employed herein in the context of dimensions (e.g. pH values, sizes, temperatures, pressures, etc.) and amounts (e.g. amounts, weights and/or concentrations of individual constituents in a composition or a component of a composition, proportions of drug inside/outside the liposomal structures, absolute doses of active ingredient, etc.), it will be appreciated that such variables are approximate and as such may vary by ±10%, for example ±5% and preferably ±2% (e.g. ±1%) from the numbers specified herein.

The compositions of the invention, and the above-mentioned process that may be employed for their preparation, have the advantages that are mentioned hereinbefore. In particular, compositions of the invention may reduce the incidence of inconvenient side-effects (and in particular irritation) that are normally observed with e.g. nasally-administered cetirizine formulations.

Compositions of the invention are easy to manufacture and enable the production of liposomal-based formulations that are in a ready-to-use form, avoiding the need for reconstitution prior to administration.

Compositions of the invention may also have the advantage that they may be prepared using established pharmaceutical processing methods and employ materials that are approved for use in foods or pharmaceuticals or of like regulatory status.

Compositions of the invention may also have the advantage that they may be more efficacious than, be less toxic than, be longer acting than, be more potent than, produce fewer side effects than, be more easily absorbed than, and/or have a better pharmacokinetic profile than, and/or have other useful pharmacological, physical, or chemical properties over, pharmaceutical compositions known in the prior art, whether for use in the treatment of rhinitis or otherwise.

The invention is illustrated by way of the following examples.

EXAMPLE 1

TABLE 1

| Batch formula | |
|---|---|
| Cetirizine dinitrate* | 22.2 g |
| Phospholipid (from soybean**) | 70.0 g |
| Disodium phosphate, dihydrate; $Na_2HPO_4\ 2H_2O$ | 21.3 g |
| Potassium dihydrogenphosphate; $KH_2PO_4$ | 11.0 g |
| 1M Hydrochloric acid and/or 1M sodium hydroxide | to pH 7.0 |
| Water for injection | to 2.0 L |

*White solid, crystallized from THF/acetonitrile/water 2:1:0.28. Obtained from commercially available cetirizine dihydrochloride via neutralisation of the free base with nitric acid.
**Lipoid S75, Lipoid GmbH, Germany General procedure. For weights and volumes reference is made to Table 1 above. A buffer solution was prepared by dissolving the buffering agents disodium phosphate dihydrate ($Na_2HPO_4 2H_2O$) and potassium dihydrogen phosphate ($KH_2PO_4$) in 1600 mL water (80% of the total batch volume) in a 2000 mL volumetric flask. The weighed amount of active agent was added to the buffer solution and dissolved by stirring with a magnetic stirrer, followed by addition of 100 mL of aqueous 1M sodium hydroxide. The phospholipid was separately weighed and added to the cetirizine solution. Stirring was continued until a well dispersed suspension had been formed, the pH of which was adjusted to pH 7.0±0.1 with 1.0 M NaOH or 1.0 M HCl. The volume of the preparation was then brought to the final batch volume of 2000 mL. The preparation was transferred to a 5 L glass vessel provided with an Ultra Turrax® T25 homogeniser (Jankel & Kühnke, Germany). Homogenisation was carried out at 22000 rpm for 3×2 minutes interrupted by 10 minute settling periods. 10 mL aliquots of the thus obtained composition were removed from the stirred dispersion and transferred to glass vials onto which spray heads (VP7 or VP7D; Valois S. A., France) were either crimped on or attached by screw fitting after filling. The stirred composition as well as the composition aliquots in the vials were protected from light.

Ultrasonication was found to further reduce mean particle size. In this method, the vials with the homogenised compositions were placed in an ultrasonication bath and sonicated for 2×10 minutes, whereupon the samples had an almost clear appearance in comparison with the opaque composition afforded by Ultra-Turrax® homogenisation.

The aforementioned particle size reduction methods are compared in Table 2. Particle size distribution was determined by laser diffraction (Mastersizer 2000, Malvern Instrument, UK). A Fraunhofer theory based method was used to calculate the particle size of the high speed homogenised sample whereas a MIE (2.50/0.001) theory based method was used for calculation of the particle size of the sample additionally subjected to sonication.

TABLE 2

Particle size reduction

| Treatment | Mean particle size (nm) |
|---|---|
| High speed homogenisation | 940 |
| High speed homogenisation + ultrasonication | 162 |

EXAMPLE 2

TABLE 3

Composition

| Cetirizine dinitrate | 2.22 g |
|---|---|
| Phospholipid (soybean; Lipoid S75; Lipoid GmbH, Germany) | 7.00 g |
| Citric acid, anhydrous | 3.84 g |
| Sodium hydroxide, solid | 1.67 g |
| Ascorbic acid | 0.20 g |
| EDTA sodium | 0.20 g |
| HCl, 1M and/or NaOH, 1M | to pH 5.0 |
| Water for injection | to 200 mL |

General procedure. For weights and volumes reference is made to Table 3. A buffer solution was prepared by dissolving anhydrous citric acid and solid sodium hydroxide in 160 mL water (80% of the total batch volume) in a 200 mL volumetric flask. The weighed amount of active agent was added and dissolved by stirring with a magnetic stirrer. The phospholipid was separately weighed and added to the cetirizine solution. Stirring was continued until a well dispersed suspension had been formed, the pH of which was adjusted to pH 5.0±0.1 with 1.0 M NaOH and/or 1.0 M HCl. The volume of the preparation was then brought to the final batch volume of 200 mL. The preparation was transferred to a high pressure homogeniser (Rannie APV, type 7.30 VH, Rannie AS, Denmark) and homogenised at 500-800 bar for 5 cycles. Aliquots of the thus obtained composition were removed from the collecting vessel and transferred to glass vials.

EXAMPLE 3

In Table 4, a high pressure homogenation particle size reduction method, as described in Example 2, is compared with high speed homogenisation (Ultra Turrax® T25 homogeniser; Jankel & Kühnke, Germany), as described in Example 1. The composition employed was that of Example 1, Particle size distribution was determined by dynamic light scattering (Zetasizer 4, Malvern Instruments, UK) at an angle of 90° and at room temperature, using a ZET5104 sizing cell and auto:CONTIN analysis mode.

TABLE 4

Particle size reduction

| Treatment | Cetirizine (mg/mL) | Z average mean (nm) |
|---|---|---|
| High speed homogenisation | 11.1 | 282 |
| High pressure homogenisation at 500 bar | 11.1 | 77 |
| High pressure homogenisation at 800 bar | 11.1 | 50 |

TABLE 4-continued

Particle size reduction

| Treatment | Cetirizine (mg/mL) | Z average mean (nm) |
|---|---|---|
| High pressure homogenisation at 500 bar | 0 | 130 |
| High pressure homogenisation at 800 bar | 0 | 121 |

The methods used for preparing these exemplary batch compositions were adapted for preparing the following additional examples.

EXAMPLE 4

| Cetirizine dinitrate | 5.6 mg |
|---|---|
| Phospholipid (soybean; Lipoid S75; Lipoid GmbH, Germany) | 35.0 mg |
| Disodium phosphate dihydrate; $Na_2HPO_4\ H_2O$ | 10.7 mg |
| Potassium dihydrogen phosphate; $KH_2PO_4$ | 5.5 mg |
| 1M HCl and/or 1M NaOH | to pH 7.0 |
| Water for injection | to 1 mL |

EXAMPLE 5

| Cetirizine dinitrate | 22.2 mg |
|---|---|
| Phospholipid (soybean; Lipoid S75; Lipoid GmbH, Germany) | 35.0 mg |
| Disodium phosphate dihydrate; $Na_2HPO_4\ H_2O$ | 10.7 mg |
| Potassium dihydrogen phosphate; $KH_2PO_4$ | 5.5 mg |
| 1M HCl and/or 1M NaOH | to pH 7.0 |
| Water for injection | to 1 mL |

EXAMPLE 6

| Cetirizine dinitrate | 11.1 mg |
|---|---|
| Phospholipid (soybean; Lipoid S75; Lipoid GmbH, Germany) | 70.0 mg |
| Disodium phosphate dihydrate; $Na_2HPO_4\ H_2O$ | 10.7 |
| Potassium dihydrogen phosphate; $KH_2PO_4$ | 5.5 mg |
| 1M HCl and/or 1M NaOH | to pH 7.0 |
| Water for injection | to 1 mL |

EXAMPLE 7

| Cetirizine dinitrate | 11.1 mg |
|---|---|
| Phospholipid (dioleoylphoshatidylcholine*) | 35.0 |
| Disodium phosphate, dihydrate; $Na_2HPO_4\ 2H_2O$ | 10.7 |
| Potassium dihydrogen phosphate; $KH_2PO_4$ | 5.5 |
| 1M HCl and/or 1M sodium hydroxide | to pH 7.0 |
| Water for injection | to 1 mL |

*DOPC, Larodan Fine Chemicals, Sweden

EXAMPLE 8

| Cetirizine dinitrate | 11.1 mg |
|---|---|
| Phospholipid (dioleoylphosphatidylglycerol*) | 35.0 mg |
| Disodium phosphate, dihydrate; $Na_2HPO_4\ 2H_2O$ | 10.7 mg |
| Potassium dihydrogen phosphate; $KH_2PO_4$ | 5.5 mg |
| 1M HCl and/or 1M sodium hydroxide | to pH 7.0 |
| Water for injection | to 1 mL |

*DOPG, Avanti Polar Lipids, AL, USA

EXAMPLE 9

| | |
|---|---|
| Cetirizine dinitrate | 11.1 mg |
| Galactolipid (digalactosyldiacylglycerol*) | 35.0 mg |
| Disodium phosphate, dihydrate; $Na_2HPO_4$ $2H_2O$ | 10.7 mg |
| Potassium dihydrogen phosphate; $KH_2PO_4$ | 5.5 mg |
| 1M HCl and/or 1M sodium hydroxide | to pH 7.0 |
| Water for injection | to 1 mL |

*DGDG, Larodan Fine Chemicals, Sweden

EXAMPLE 10

Nasal Irritation Test in a Dog Model

Cetirizine dinitrate (5.6, 11.1 and 22.2 mg/mL, respectively, in the compositions of Examples 1, 4 and 5; shaken rather than high speed or high pressure homogenised) was administered twice daily for 14 days to four male beagle dogs per group (5-6 months old, weighing 10.1-14.2 kg). Clinical signs and body weights were monitored throughout the study. A necropsy was performed, and the nasal cavity was collected and processed (fixated, decalcified and stained with haematoxylin and eosin). Four sections from the nasal cavity were evaluated microscopically, covering squamous, ciliated respiratory, and olfactory epithelium. No treatment-related clinical signs were observed during the administration period. The mean body weight gain over the administration period was unremarkable. The macroscopic and microscopic examination of the nasal cavity and the nasal mucosa preparations did not reveal any signs of mucosal irritation or other change.

EXAMPLE 11

Ocular Irritation Test in a Rabbit Model

The potential irritating properties of the compositions of the invention was also assessed in an eye irritation test in three white (albino), female New Zealand rabbits per treatment weighing between 2.8 to 3.4 kg. The concentrations investigated were 5.6, 11.1 and 22.2 mg/mL in the composition of Example 1. 0.1 mL of the composition was placed in the left eye of each rabbit. The right eye served as untreated control. The eyes were examined prior to treatment and at 1, 24, 48, and 72 h after treatment. The ocular reaction to treatment was graded according to a subjective numerical scoring system. Signs of conjunctival irritation (redness) were observed in two rabbits in the group receiving the composition containing 22.2 mg/mL cetirizine dinitrate. In the first rabbit, a score 2 (diffuse, crimson colour, individual vessels not easily discernable) on a scale graded 0 to 3 was noted one hour after treatment. In the second rabbit, a score 1 (some hyperaemic blood vessels) on a four grade scale was noted at 24 h. In both cases the redness was not present at subsequent observations, and was thus considered reversible. No other signs of eye irritation were observed in any of the animals.

EXAMPLE 12

Nasal Irritation Test

A single dose (110 μL in each nostril) of cetirizine dinitrate (11.1 mg/mL) was administered to five healthy volunteers at four sessions in one of four formulations (I-IV; see Table 5 for details) in each session. Formulations I, II and III are formulations of the examples above whereas reference formulation IV was not a formulation of the invention. The test was performed to investigate the reduction of irritation by liposome formulation as compared to plain buffer solution. Also the influence of particle size and the ratio phospholipid to cetirizine was studied.

TABLE 5

Cetirizine Dinitrate Formulations Used in Testing Nasal Irritation

| Formulation | Composition | mg Phospholipid per mL Vehicle | Features* |
|---|---|---|---|
| I | Example 1 | 35 | High speed homogenised |
| II | Example 1 | 35 | High speed homogenised + ultrasonicated |
| III | Example 6 | 70 | High speed homogenised + ultrasonicated |
| IV | Reference | nil; phosphate buffer | Plain buffered aqueous solution |

*Refer to Table 2

Nasal symptom score were assessed at 1, 10, 30 minutes post administration. The nasal symptom score included the following variables: nasal congestion, rhinorrhea, itching/sneezing, burning/pain, and taste. These symptoms were qualified by the subjects according to a no—mild—moderate—severe symptom scale (0-3). The results are reported as total score, adding all five subjects scores (maximum score of 15).

The phospholipid formulations were better tolerated than the plain buffer solution. Smaller liposomes seem to be of some advantage. The mild discomfort reported by all subjects at 1 minute had practically disappeared at 10 min for the two formulations (II and III) that had reduced particle size by sonication. In contrast, the initial mild discomfort reported for formulation I persisted at 10 minutes. Increasing the ratio of phospholipid to cetirizine did not further improve the performance of the formulation.

TABLE 6

Nasal irritation test in healthy volunteers

| Formulation | Congestion | Rhinorrhea | Itching/sneezing | Burning/Pain | Taste | TOTAL SCORE |
|---|---|---|---|---|---|---|
| 1 minute post-administration ||||||| 
| I | 0 | 3 | 1 | 6.5 | 1 | 11.5 |
| II | 0 | 1 | 1 | 6 | 0 | 8 |
| III | 0 | 0 | 1 | 5.5 | 0 | 6.5 |
| IV | 0 | 6 | 2 | 14.5 | 2 | 24.5 |
| 10 minutes post-administration ||||||| 
| I | 0 | 1 | 1 | 6 | 4 | 12 |
| II | 0 | 0 | 0 | 2 | 2 | 4 |
| III | 0 | 0 | 1 | 1 | 4.5 | 6.5 |
| IV | 0 | 1 | 1 | 8 | 3 | 13 |
| 30 minutes post-administration ||||||| 
| I | 0 | 0 | 1 | 1 | 3 | 5 |
| II | 0 | 0 | 1 | 0 | 0 | 1 |
| III | 0 | 0 | 0 | 1 | 1 | 2 |
| IV | 0 | 0 | 0 | 1.5 | 1 | 2.5 |

EXAMPLE 13

Nasal Irritation Test

A single dose (110 μL in each nostril) of cetirizine dinitrate (11.1 mg/mL) was administered to four healthy volunteers, at four sessions in one of four formulations (I-IV;

see Table 7 for details) in each session. The test was performed to investigate the irritative properties of formulations with different membrane lipids of natural and synthetic origin.

TABLE 7

Cetirizine dinitrate formulations used in testing nasal irritation

| Formulation | Composition | Membrane lipid | |
|---|---|---|---|
| I | Example 1 | Lipoid S75 | Natural |
| II | Example 7 | Dioleoylphoshatidylcholine (DOPC) | Synthetic |
| III | Example 8 | Dioleoylphoshatidylglycerol (DOPG) | Synthetic |
| IV | Example 9 | Digalactosyldiacylglycerol (DGDG) | Natural |

Nasal symptom score were assessed at 1, 10, 30 minutes post administration. The nasal symptom score included the following variables: nasal congestion, rhinorrhea, itching/sneezing, burning/pain, and taste. These symptoms were qualified by the subjects according to a no—mild—moderate—severe symptom scale (0-3). The results are reported as total score, adding all four subjects scores (maximum score of 12).

The formulations containing DOPC and DOPG were very well tolerated with practically no reports of any kind at 1 minute. At 10 minutes there was still a tendency of better tolerability of these two formulations as compared to the membrane lipids of natural origin.

TABLE 8

Nasal irritation test in healthy volunteers

| Formulation | Congestion | Rhinorrhea | Itching/sneezing | Burning/Pain | Taste | TOTAL SCORE |
|---|---|---|---|---|---|---|
| 1 minute post-administration ||||||||
| I | 0 | 1 | 1 | 3 | 2 | 7 |
| II | 0 | 1 | 0 | 1 | 0 | 2 |
| III | 1 | 0 | 1 | 0 | 0 | 1 |
| IV | 0 | 1.5 | 2 | 2 | 4 | 9.5 |
| 10 minutes post-administration ||||||||
| I | 0 | 1 | 0 | 2 | 3 | 6 |
| II | 0 | 0 | 0 | 1 | 2 | 3 |
| III | 0 | 0.5 | 0.5 | 1 | 2 | 4 |
| IV | 0.5 | 0.5 | 0 | 1 | 4 | 6 |
| 30 minutes post-administration ||||||||
| I | 1 | 0 | 0 | 0 | 0 | 1 |
| II | 0 | 0 | 0 | 0 | 0 | 0 |
| III | 0 | 0 | 1 | 0 | 1 | 2 |
| IV | 0 | 0 | 0 | 0 | 0 | 0 |

The following examples were also made in accordance with procedures analogous to those described hereinbefore.

EXAMPLE 14

| | |
|---|---|
| Cetirizine dinitrate | 11.1 mg |
| Phospholipid (soybean; Lipoid S100; Lipoid GmbH, Germany) | 35.0 mg |
| Citric acid | 19.2 mg |
| Sodium hydroxide | 8.4 mg |
| 1M HCl and/or 1M NaOH | to pH 5.5 |
| Water for injection | to 1 mL |

EXAMPLE 15

| | |
|---|---|
| Cetirizine dinitrate | 11.1 mg |
| Phospholipid (soybean; Lipoid S100; Lipoid GmbH, Germany) | 50.0 mg |
| Citric acid | 19.2 mg |
| Sodium hydroxide | 8.4 mg |
| 1M HCl and/or 1M NaOH | to pH 5.5 |
| Water for injection | to 1 mL |

EXAMPLE 16

| | |
|---|---|
| Cetirizine dinitrate | 11.1 mg |
| Phospholipid (soybean; Lipoid S100; Lipoid GmbH, Germany) | 35.0 mg |
| EDTA | 0.1 mg |
| Citric acid | 19.2 mg |
| Sodium hydroxide | 8.4 mg |
| 1M HCl and/or 1M NaOH | to pH 5.5 |
| Water for injection | to 1 mL |

EXAMPLE 17

| | |
|---|---|
| Cetirizine dinitrate | 11.1 mg |
| Phospholipid (soybean; Lipoid S100; Lipoid GmbH, Germany) | 35.0 mg |
| Benzalkonium chloride | 0.1 mg |
| Citric acid | 19.2 mg |
| Sodium hydroxide | 8.4 mg |
| 1M HCl and/or 1M NaOH | to pH 5.5 |
| Water for injection | to 1 mL |

EXAMPLE 18

| | |
|---|---|
| Cetirizine dinitrate | 11.1 mg |
| Phospholipid (soybean; Lipoid S100; Lipoid GmbH, Germany) | 35.0 mg |
| Methylparaben | 1.8 mg |
| Propylparaben | 0.2 mg |
| Citric acid | 19.2 mg |
| Sodium hydroxide | 8.4 mg |
| 1M HCl and/or 1M NaOH | to pH 5.5 |
| Water for injection | to 1 mL |

EXAMPLE 19

| | |
|---|---|
| Cetirizine dinitrate | 11.1 mg |
| Phospholipid (soybean; Lipoid S100; Lipoid GmbH, Germany) | 35.0 mg |
| Butylated hydroxytoluene (BHT) | 0.1 mg |
| Citric acid | 19.2 mg |
| Sodium hydroxide | 8.4 mg |
| 1M HCl and/or 1M NaOH | to pH 5.5 |
| Water for injection | to 1 mL |

EXAMPLE 20

| | |
|---|---|
| Cetirizine dinitrate | 11.1 mg |
| Phospholipid (soybean; Lipoid S100; Lipoid GmbH, Germany) | 23.3 mg |
| Phospholipid (soybean; Lipoid S75-3 N; Lipoid GmbH, Germany) | 11.7 mg |
| Citric acid | 19.2 mg |
| Sodium hydroxide | 8.4 mg |
| 1M HCl and/or 1M NaOH | to pH 5.5 |
| Water for injection | to 1 mL |

EXAMPLE 21

| | |
|---|---|
| Cetirizine dinitrate | 11.1 mg |
| Phospholipid (soybean; Lipoid S100; Lipoid GmbH, Germany) | 11.7 mg |
| Phospholipid (DMPC; Lipoid GmbH, Germany) | 23.3 mg |
| Citric acid | 19.2 mg |
| Sodium hydroxide | 8.4 mg |
| 1M HCl and/or 1M NaOH | to pH 5.5 |
| Water for injection | to 1 mL |

EXAMPLE 22

| | |
|---|---|
| Cetirizine dinitrate | 11.1 mg |
| Phospholipid (soybean; Lipoid S100; Lipoid GmbH, Germany) | 17.5 mg |
| Phospholipid (DMPC; Lipoid GmbH, Germany) | 17.5 mg |
| Citric acid | 19.2 mg |
| Sodium hydroxide | 8.4 mg |
| 1M HCl and/or 1M NaOH | to pH 5.5 |
| Water for injection | to 1 mL |

EXAMPLE 23

| | |
|---|---|
| Cetirizine dinitrate | 11.1 mg |
| Phospholipid (soybean; Lipoid S100; Lipoid GmbH, Germany) | 23.3 mg |
| Phospholipid (DMPC; Lipoid GmbH, Germany) | 11.7 mg |
| Citric acid | 19.2 mg |
| Sodium hydroxide | 8.4 mg |
| 1M HCl and/or 1M NaOH | to pH 5.5 |
| Water for injection | to 1 mL |

EXAMPLE 24

| | |
|---|---|
| Cetirizine dinitrate | 11.1 mg |
| Phospholipid (soybean; Lipoid S100; Lipoid GmbH, Germany) | 35.0 mg |
| Hydroxypropylmethylcellulose (Metolose 60SH-50) | 1.0 mg |
| Citric acid | 19.2 mg |
| Sodium hydroxide | 8.4 mg |
| 1M HCl and/or 1M NaOH | to pH 5.5 |
| Water for injection | to 1 mL |

EXAMPLE 25

| | |
|---|---|
| Cetirizine dinitrate | 11.1 mg |
| Phospholipid (soybean; Lipoid S100; Lipoid GmbH, Germany) | 35.0 mg |
| Polyethylene glycol (Macrogol 6000) | 1.0 mg |
| Citric acid | 19.2 mg |
| Sodium hydroxide | 8.4 mg |
| 1M HCl and/or 1M NaOH | to pH 5.5 |
| Water for injection | to 1 mL |

EXAMPLE 26

| | |
|---|---|
| Cetirizine dinitrate | 11.1 mg |
| Phospholipid (soybean; Lipoid S100; Lipoid GmbH, Germany) | 35.0 mg |
| Benzalkonium chloride | 0.1 mg |
| Butylated hydroxytoluene (BHT) | 0.1 mg |
| Citric acid | 19.2 mg |
| Sodium hydroxide | 8.4 mg |
| 1M HCl and/or 1M NaOH | to pH 5.5 |
| Water for injection | to 1 mL |

EXAMPLE 27

| | |
|---|---|
| Cetirizine dinitrate | 11.1 mg |
| Phospholipid (soybean; Lipoid S100; Lipoid GmbH, Germany) | 35.0 mg |
| Benzalkonium chloride | 0.1 mg |
| Butylated hydroxytoluene (BHT) | 0.1 mg |
| Hydroxypropylmethylcellulose (Metolose 60SH-50) | 10 mg |
| Citric acid | 19.2 mg |
| Sodium hydroxide | 8.4 mg |
| 1M HCl and/or 1M NaOH | to pH 5.5 |
| Water for injection | to 1 mL |

EXAMPLE 28

| | |
|---|---|
| Cetirizine dinitrate | 11.1 mg |
| Phospholipid (soybean; Lipoid S100; Lipoid GmbH, Germany) | 17.5 mg |
| Phospholipid (DMPC; Lipoid GmbH, Germany) | 17.5 mg |
| Benzalkonium chloride | 0.1 mg |
| Butylated hydroxytoluene (BHT) | 0.1 mg |
| Citric acid | 19.2 mg |
| Sodium hydroxide | 8.4 mg |
| 1M HCl and/or 1M NaOH | to pH 5.5 |
| Water for injection | to 1 mL |

EXAMPLE 29

| | |
|---|---|
| Cetirizine dinitrate | 11.1 mg |
| Phospholipid (soybean; Lipoid S100; Lipoid GmbH, Germany) | 23.3 mg |
| Phospholipid (DMPC; Lipoid GmbH, Germany) | 11.7 mg |
| Benzalkonium chloride | 0.1 mg |
| Butylated hydroxytoluene (BHT) | 0.1 mg |
| Citric acid | 19.2 mg |
| Sodium hydroxide | 8.4 mg |
| 1M HCl and/or 1M NaOH | to pH 5.5 |
| Water for injection | to 1 mL |

EXAMPLE 30

| | |
|---|---|
| Cetirizine dinitrate | 11.1 mg |
| Phospholipid (soybean; Lipoid S100; Lipoid GmbH, Germany) | 23.3 mg |
| Phospholipid (DMPC; Lipoid GmbH, Germany) | 11.7 mg |
| Benzalkonium chloride | 0.1 mg |
| Butylated hydroxytoluene (BHT) | 0.1 mg |
| Polyethylene glycol (Macrogol 6000) | 10 mg |
| Citric acid | 19.2 mg |
| Sodium hydroxide | 8.4 mg |
| 1M HCl and/or 1M NaOH | to pH 5.5 |
| Water for injection | to 1 mL |

EXAMPLE 31

| | |
|---|---|
| Cetirizine dinitrate | 11.1 mg |
| Phospholipid (soybean; Lipoid S100; Lipoid GmbH, Germany) | 29.2 mg |
| Phospholipid (DMPC; Lipoid GmbH, Germany | 5.8 mg |
| Benzalkonium chloride | 0.1 mg |
| Butylated hydroxytoluene (BHT) | 0.01 mg |
| Povidone | 1.0 mg |
| Citric acid | 19.2 mg |
| Sodium hydroxide | 8.4 mg |
| 1M HCl and/or 1M NaOH | to pH 5.5 |
| Water for injection | to 1 mL |

EXAMPLE 32

| | |
|---|---|
| Cetirizine dinitrate | 11.1 mg |
| Phospholipid (soybean; Lipoid S100; Lipoid GmbH, Germany) | 23.3 mg |
| Phospholipid (DMPC; Lipoid GmbH, Germany) | 11.7 mg |
| Benzalkonium chloride | 1.0 mg |
| Butylated hydroxytoluene (BHT) | 0.1 mg |
| Hydroxypropylmethylcellulose (Metolose 60SH-50) | 5.0 mg |
| Citric acid | 19.2 mg |
| Sodium hydroxide | 8.4 mg |
| 1M HCl and/or 1M NaOH | to pH 5.5 |
| Water for injection | to 1 mL |

EXAMPLE 33

| | |
|---|---|
| Cetirizine dihydrochloride | 11.1 mg |
| Phospholipid (soybean; Lipoid S100; Lipoid GmbH, Germany) | 35.0 mg |
| Ascorbic acid | 1.0 mg |
| Citric acid | 19.2 mg |
| Sodium hydroxide | 8.4 mg |
| 1M HCl and/or 1M NaOH | to pH 5.5 |
| Water for injection | to 1 mL |

EXAMPLE 34

| | |
|---|---|
| Cetirizine dihydrochloride | 11.1 mg |
| Phospholipid (soybean; Lipoid S100; Lipoid GmbH, Germany) | 35.0 mg |
| α-Tocopherol | 1.0 mg |
| Citric acid | 19.2 mg |
| Sodium hydroxide | 8.4 mg |
| 1M HCl and/or 1M NaOH | to pH 5.5 |
| Water for injection | to 1 mL |

EXAMPLE 35

| | |
|---|---|
| Cetirizine dihydrochloride | 11.1 mg |
| Phospholipid (soybean; Lipoid S100; Lipoid GmbH, Germany) | 35.0 mg |
| Butylated hydroxytoluene (BHT) | 0.1 mg |
| Citric acid | 19.2 mg |
| Sodium hydroxide | 8.4 mg |
| 1M HCl and/or 1M NaOH | to pH 5.5 |
| Water for injection | to 1 mL |

What is claimed is:

1. A method for the treatment of rhinitis comprising the administration of a pharmaceutical composition comprising zwitterionic cetirizine, a polar lipid liposome and a pharmaceutically-acceptable aqueous carrier, wherein the concentration of zwitterionic cetirizine is substantially similar in the aqueous carrier both within and surrounding the liposomes, and the diameter of the liposomes is less than about 200 nm to a person suffering from or susceptible to that disorder.

2. A method as claimed in claim 1, wherein the administration is intranasal.

3. A method as claimed in claim 1, wherein the administration is intraocular.

* * * * *